(12) United States Patent
Tsuji et al.

(10) Patent No.: US 12,740,841 B2
(45) Date of Patent: Sep. 22, 2026

(54) COMPUTER-ASSISTED TELEOPERATED SURGERY SYSTEMS AND METHODS

(71) Applicant: INTUITIVE SURGICAL OPERATIONS, INC., Sunnyvale, CA (US)

(72) Inventors: Craig Keith Tsuji, San Jose, CA (US); Edward Paul Donlon, San Jose, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 219 days.

(21) Appl. No.: 18/545,544

(22) Filed: Dec. 19, 2023

(65) Prior Publication Data

US 2024/0189055 A1 Jun. 13, 2024

Related U.S. Application Data

(63) Continuation of application No. 16/644,326, filed as application No. PCT/US2018/049101 on Aug. 31, 2018, now Pat. No. 11,896,334.

(60) Provisional application No. 62/554,254, filed on Sep. 5, 2017.

(51) Int. Cl.

| | |
|---|---|
| ***A61B 34/00*** | (2016.01) |
| ***A61B 17/00*** | (2006.01) |
| ***A61B 34/35*** | (2016.01) |

(52) U.S. Cl.

CPC ............. *A61B 34/71* (2016.02); *A61B 34/35* (2016.02); *A61B 2017/00314* (2013.01); *A61B 2017/00327* (2013.01)

(58) Field of Classification Search

CPC ........... A61B 2017/00314; A61B 2017/00327; A61B 2017/2927; A61B 2034/305; A61B 34/00; A61B 34/30; A61B 34/35; A61B 34/71

See application file for complete search history.

(56) References Cited

U.S. PATENT DOCUMENTS

| | | | |
|---|---|---|---|
| 5,710,870 A | 1/1998 | Ohm et al. | |
| 2006/0199999 A1* | 9/2006 | Ikeda | A61B 34/71 600/141 |
| 2007/0219581 A1 | 9/2007 | Dohi et al. | |
| 2011/0118708 A1 | 5/2011 | Burbank et al. | |
| 2014/0236175 A1 | 8/2014 | Cooper et al. | |
| 2016/0166346 A1* | 6/2016 | Kostrzewski | F16D 1/08 606/130 |

(Continued)

OTHER PUBLICATIONS

International Preliminary Report on Patentability for Application No. PCT/US2018/049101, mailed on Mar. 19, 2020, 9 pages.

(Continued)

*Primary Examiner* — Mohamed G Gabr

(74) *Attorney, Agent, or Firm* — Jones Burke, PLLC

(57) ABSTRACT

A joint mechanism includes a first end joint member; a middle joint member; a second end joint member; a first linkage member comprising a first annular band, the first linkage member pivotably coupled with the first end joint member and pivotably coupled with the middle joint member; and a second linkage member comprising a second annular band, the second linkage member pivotably coupled with the middle joint member and pivotably coupled with the second end joint member.

20 Claims, 7 Drawing Sheets

(56) References Cited

U.S. PATENT DOCUMENTS

| | | | |
|---|---|---|---|
| 2017/0021507 | A1 | 1/2017 | Jackson et al. |
| 2021/0022818 | A1 | 1/2021 | Tsuji et al. |

OTHER PUBLICATIONS

International Search Report and Written Opinion for Application No. PCT/US2018/049101, mailed Feb. 8, 2019, 12 pages.

Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

COMPUTER-ASSISTED TELEOPERATED SURGERY SYSTEMS AND METHODS

CROSS-REFERENCE TO RELATED APPLICATION

This application is a continuation of U.S. patent application Ser. No. 16/644,326, which is a is a National Stage Application under 35 U.S.C. § 371 and claims the benefit of International Application No. PCT/US2018/049101, filed Aug. 31, 2018, which claims benefit of U.S. Provisional Application No. 62/554,254, filed Sep. 5, 2017 (now expired), each of which is hereby incorporated by reference in their entirety.

TECHNICAL FIELD

This disclosure relates to devices and methods for minimally invasive computer-assisted teleoperated surgery. For example, this disclosure relates to computer-assisted teleoperated surgery instruments with cable-actuated joint mechanisms.

BACKGROUND

Robotic systems and computer-assisted devices often include robot or movable arms to manipulate instruments for performing a task at a work site and at least one robot or movable arm for supporting an image capturing device which captures images of the work site. A robot arm comprises a plurality of links coupled together by one or more actively controlled joints. In many embodiments, a plurality of actively controlled joints may be provided. The robot arm may also include one or more passive joints, which are not actively controlled, but comply with movement of an actively controlled joint. Such active and passive joints may be revolute or prismatic joints. The configuration of the robot arm may then be determined by the positions of the joints and knowledge of the structure and coupling of the links.

Minimally invasive telesurgical systems for use in surgery are being developed to increase a surgeon's dexterity as well as to allow a surgeon to operate on a patient from a remote location. Telesurgery is a general term for surgical systems where the surgeon uses some form of remote control, e.g., a servomechanism, or the like, to manipulate surgical instrument movements rather than directly holding and moving the instruments by hand. In such a telesurgery system, the surgeon is provided with an image of the surgical site at the remote location. While viewing typically a three-dimensional image of the surgical site on a suitable viewer or display, the surgeon performs the surgical procedures on the patient by manipulating master control input devices, which in turn control the motion of robotic instruments. The robotic surgical instruments can be inserted through small, minimally invasive surgical apertures to treat tissues at surgical sites within the patient, often avoiding the trauma generally associated with accessing a surgical worksite by open surgery techniques. These robotic systems can move the working ends of the surgical instruments with sufficient dexterity to perform quite intricate surgical tasks, often by pivoting shafts of the instruments at the minimally invasive aperture, sliding of the shaft axially through the aperture, rotating of the shaft within the aperture, and/or the like.

SUMMARY

This disclosure describes devices and methods for minimally invasive robotic surgery using a computer-assisted teleoperated medical device. For example, this disclosure describes computer-assisted teleoperated surgery instruments with cable-actuated joint mechanisms. Some such joint mechanisms include linkages that hold the joints in operable configurations without relying on cable tension to do so. The devices and methods provided herein can be used in conjunction with robotic surgery systems that use either hardware-constrained remote centers of motion or software-constrained remote centers of motion.

In one aspect, this disclosure is directed to joint mechanism that includes a first end joint member; a middle joint member; a second end joint member; a first linkage member; and a second linkage member. The first linkage member comprises a first annular band. The first linkage member is pivotably coupled with the first end joint member and pivotably coupled with the middle joint member. The second linkage member comprises a second annular band. The second linkage member is pivotably coupled with the middle joint member and pivotably coupled with the second end joint member.

Such a joint mechanism may optionally include one or more of the following features. The first and second end joint members may be constrained by the first and second linkage members to pivot in relation to middle joint member along respective paths that are orthogonal to each other. One or both of the first and second linkage members may be unitary components. The first linkage member may also include: a first pair of bosses that protrude from the first annular band; and a second pair of bosses that protrude from the first annular band. The second linkage member may also include: a third pair of bosses that protrude from the second annular band; and a fourth pair of bosses that protrude from the second annular band. One or more boss of the first pair of bosses, second pair of bosses, third pair of bosses, and fourth pair of bosses may include a feature to pivotably couple with a respective joint member of the first end joint member, middle joint member, and second end joint member. The feature may be a hole. The feature may be a protrusion. The joint mechanism may define a passage extending through each of the first end joint member, the middle joint member, the second end joint member, the first linkage member, and second linkage member.

In another aspect, this disclosure is directed to a surgical instrument, that includes an elongate shaft; a joint mechanism; and a surgical tool coupled to a second end of the joint mechanism. A first end of the joint member is coupled to a distal end of the elongate shaft. The joint mechanism includes: a first end joint member; a middle joint member; a second end joint member; a first linkage member comprising a first annular band, the first linkage member pivotably coupled with the first end joint member and pivotably coupled with the middle joint member; and a second linkage member comprising a second annular band, the second linkage member pivotably coupled with the middle joint member and pivotably coupled with the second end joint member.

Such a surgical instrument may optionally include one or more of the following features. The surgical instrument may also include four cable portions extending along the elongate shaft and affixed to the second end joint member. The surgical instrument may also include two capstans disposed at a proximal end of the elongate shaft. Each of the cable portions may be engaged with a respective one of the capstans. Each of the cable portions may extend through passages defined by each one of the first end joint member and the middle joint member. The joint mechanism may remain intact while the four cable portions are not under any tension. The surgical tool may be a suction and irrigation device. A passage may be defined that extends through each of the elongate shaft, the first end joint member, the middle joint member, the second end joint member, the first linkage member, and second linkage member.

In another aspect, this disclosure is directed to a joint mechanism that includes: a first end joint member including a first pair of protrusions; a middle joint member including a second pair of protrusions and a third pair of protrusions; a second end joint member including a fourth pair of protrusions; a first linkage member comprising an annular band and defining a first pair of holes and a second pair of holes, the first pair of holes pivotably mated with the first pair of protrusions, the second pair of holes pivotably mated with the second pair of protrusions; and a second linkage member comprising an annular band and defining a third pair of holes and a fourth pair of holes, the third pair of holes pivotably mated with the third pair of protrusions, the fourth pair of holes pivotably mated with the fourth pair of protrusions.

Such a joint mechanism may optionally include one or more of the following features. The first linkage member may include: a first pair of bosses that protrude from the first annular band and that define the first pair of holes; and a second pair of bosses that protrude from the first annular band and that define the second pair of holes. The second linkage member may include: a third pair of bosses that protrude from the second annular band and that define the third pair of holes; and a fourth pair of bosses that protrude from the second annular band and that define the fourth pair of holes. The first and second end joint members may be constrained by the first and second linkage members to pivot in relation to middle joint member along respective paths that are orthogonal to each other. The joint mechanism may define a passage extending through each of the first end joint member, the middle joint member, the second end joint member, the first linkage member, and second linkage member. One or both of the first and second linkage members may be unitary components.

Some or all of the embodiments described herein may provide one or more of the following advantages. In some cases, the robotic surgery devices and methods provided herein facilitate manipulation of an end effector about two perpendicular pivot axes of a joint mechanism. For example, such a joint mechanism may include elements that have gear teeth members. The gears permit pivotal movement of the joint members of the joint mechanism, while preventing lateral movement (e.g., lateral separation) of the joint members. Owing to certain contact points between the gear teeth, as the joint members pivot with respect to each other, a first proximal end of a cable that secures the joint mechanism to a surgical device is paid out (e.g., extended distally) by a capstan, while a second proximal end of the same cable is pulled in (e.g., pulled proximally) by the capstan, such that a total operational length of the cable is maintained to effect link conservation. Accordingly, the cable is protected from failing (e.g., excessive stretching or breaking) in tension during movements of the joint mechanisms.

In another advantageous aspect, linkage members of the joint mechanism maintain engagement between gear teeth of the adjoining joint members such that at any orientations of the joint members, contact between the linkage members and the joint members can counteract forces that may be exerted during use of the surgical instrument. The joint mechanism designs can thereby prevent lateral and axial movements of the joint members with respect to each other (e.g., prevent "dislocation" of joint members) without relying on cable tension.

The details of one or more embodiments are set forth in the accompanying drawings and the description below. Other features, objects, and advantages will be apparent from the description and drawings, and from the claims.

BRIEF DESCRIPTION OF THE DRAWINGS

Like reference symbols in the various drawings indicate like elements.

DETAILED DESCRIPTION

Figures 1, 2:
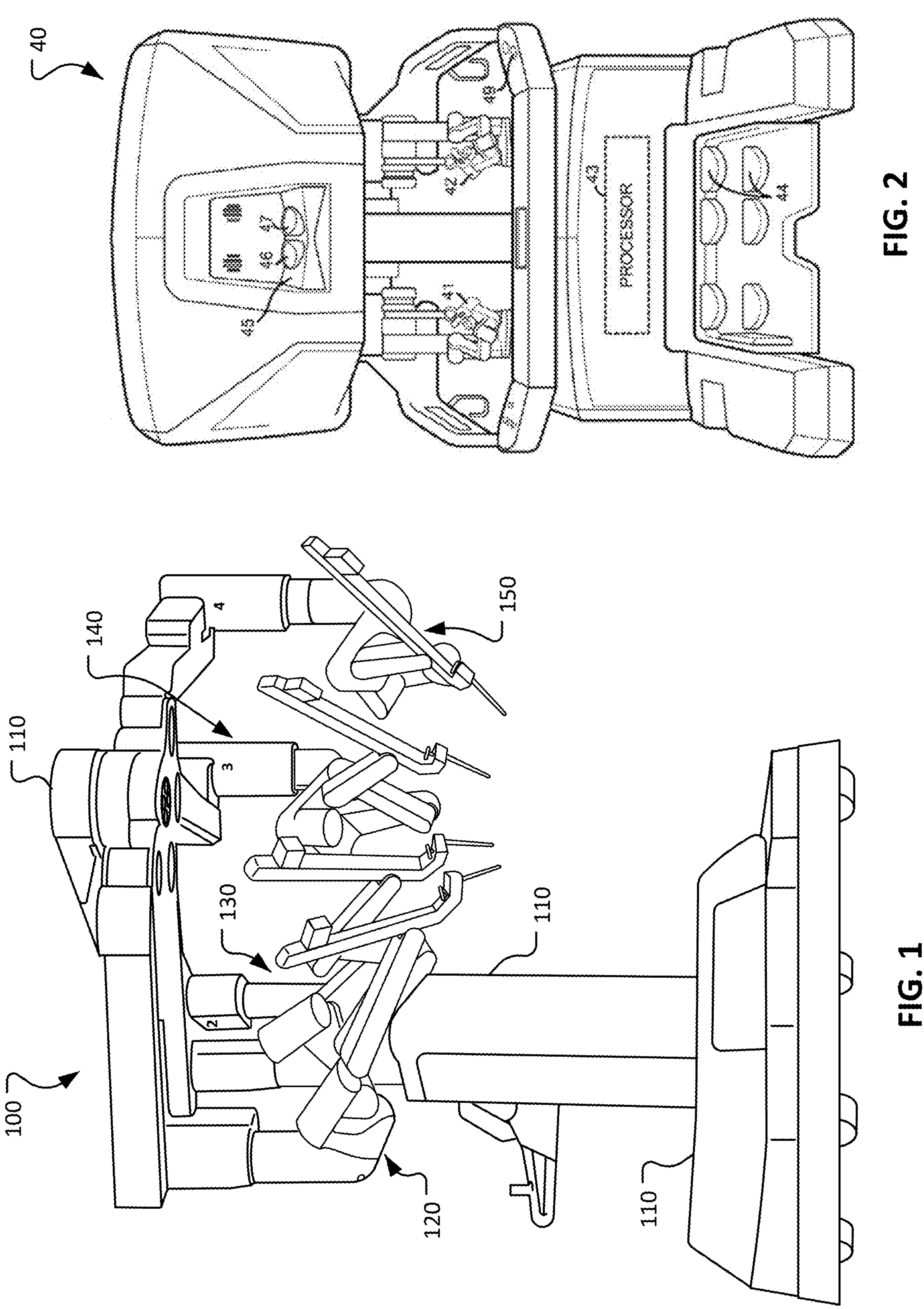
FIG. 1 is a perspective view of an example patient-side cart of a computer-assisted teleoperated surgery system.
FIG. 2 is a front view of an example surgeon console of a computer-assisted teleoperated surgery system.

This description and the accompanying drawings that illustrate inventive aspects, embodiments, implementations, or applications should not be taken as limiting—the claims define the protected invention. Various mechanical, compositional, structural, electrical, and operational changes may be made without departing from the spirit and scope of this description and the claims. In some instances, well-known circuits, structures, or techniques have not been shown or described in detail in order not to obscure the invention. Like numbers in two or more figures represent the same or similar elements.

Further, specific words chosen to describe one or more embodiments and optional elements or features are not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., translational placements) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (e.g., rotated 90 degrees or at other orientations) and the spatially relative descriptors used herein interpreted accordingly. Likewise, descriptions of movement along (translation) and around (rotation) various axes includes various special device positions and orientations. The combination of a body's position and orientation define the body's pose.

Similarly, geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round", a component that is not precisely circular (e.g., one that is slightly oblong or is a many-sided polygon) is still encompassed by this description. The words "including" or "having" mean including but not limited to.

It should be understood that although this description is made to be sufficiently clear, concise, and exact, scrupulous and exhaustive linguistic precision is not always possible or desirable, since the description should be kept to a reasonable length and skilled readers will understand background and associated technology. For example, considering a video signal, a skilled reader will understand that an oscilloscope described as displaying the signal does not display the signal itself but a representation of the signal, and that a video monitor described as displaying the signal does not display the signal itself but video information the signal carries.

In addition, the singular forms "a", "an", and "the" are intended to include the plural forms as well, unless the context indicates otherwise. And, the terms "comprises", "includes", "has", and the like specify the presence of stated features, steps, operations, elements, and/or components but do not preclude the presence or addition of one or more other features, steps, operations, elements, components, and/or groups. And, the or each of the one or more individual listed items should be considered optional unless otherwise stated, so that various combinations of items are described without an exhaustive list of each possible combination. The auxiliary verb may likewise implies that a feature, step, operation, element, or component is optional.

Elements described in detail with reference to one embodiment, implementation, or application optionally may be included, whenever practical, in other embodiments, implementations, or applications in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions.

Elements described as coupled may be electrically or mechanically directly coupled, or they may be indirectly coupled via one or more intermediate components.

The term "flexible" in association with a part, such as a mechanical structure, component, or component assembly, should be broadly construed. In essence, the term means the part can be repeatedly bent and restored to an original shape without harm to the part. Many "rigid" objects have a slight inherent resilient "bendiness" due to material properties, although such objects are not considered "flexible" as the term is used herein. A flexible part may have infinite degrees of freedom (DOF's). Examples of such parts include closed, bendable tubes (made from, e.g., NITINOL, polymer, soft rubber, and the like), helical coil springs, etc. that can be bent into various simple or compound curves, often without significant cross-sectional deformation. Other flexible parts may approximate such an infinite-DOF part by using a series of closely spaced components that are similar to a snake-like arrangement of serial "vertebrae." In such a vertebral arrangement, each component is a short link in a kinematic chain, and movable mechanical constraints (e.g., pin hinge, cup and ball, live hinge, and the like) between each link may allow one (e.g., pitch) or two (e.g., pitch and yaw) DOF's of relative movement between the links. A short, flexible part may serve as, and be modeled as, a single mechanical constraint (joint) that provides one or more DOF's between two links in a kinematic chain, even though the flexible part itself may be a kinematic chain made of several coupled links. Knowledgeable persons will understand that a part's flexibility may be expressed in terms of its stiffness.

Unless otherwise stated in this description, a flexible part, such as a mechanical structure, component, or component assembly, may be either actively or passively flexible. An actively flexible part may be bent by using forces inherently associated with the part itself. For example, one or more tendons may be routed lengthwise along the part and offset from the part's longitudinal axis, so that tension on the one or more tendons causes the part or a portion of the part to bend. Other ways of actively bending an actively flexible part include, without limitation, the use of pneumatic or hydraulic power, gears, electroactive polymer (more generally, "artificial muscle"), and the like. A passively flexible part is bent by using a force external to the part (e.g., an applied mechanical or electromagnetic force). A passively flexible part may remain in its bent shape until bent again, or it may have an inherent characteristic that tends to restore the part to an original shape. An example of a passively flexible part with inherent stiffness is a plastic rod or a resilient rubber tube. An actively flexible part, when not actuated by its inherently associated forces, may be passively flexible. A single part may be made of one or more actively and passively flexible parts in series.

Aspects of the invention are described primarily in terms of an implementation using a da Vinci® Surgical System, commercialized by Intuitive Surgical, Inc. of Sunnyvale, California. Examples of such surgical systems are the da Vinci® Xi™ Surgical System (Model IS4000) and the da Vinci® Si™ HD™ Surgical System (Model IS3000). Knowledgeable persons will understand, however, that inventive aspects disclosed herein may be embodied and implemented in various ways, including computer-assisted, non-computer-assisted, and hybrid combinations of manual and computer-assisted embodiments and implementations.

Implementations on da Vinci® Surgical Systems (e.g., the Model IS4000, the Model IS3000, the Model IS2000, the Model IS1200) are merely exemplary and are not to be considered as limiting the scope of the inventive aspects disclosed herein. As applicable, inventive aspects may be embodied and implemented in both relatively smaller, hand-held, hand-operated devices and relatively larger systems that have additional mechanical support, as well as in other embodiments of computer-assisted teleoperated medical devices.

It should be understood that the diminutive scale of the disclosed structures and mechanisms creates unique mechanical conditions and difficulties with the construction of these structures and mechanisms that are unlike those found in similar structures and mechanisms constructed at a larger scale, because forces and strengths of materials do not scale at the same rate as the size of the mechanisms. For example, a surgical instrument having an 8 mm shaft diameter cannot simply be scaled down to a 5 mm shaft diameter due to mechanical, material property, and manufacturing considerations. Likewise, a 5 mm shaft diameter device cannot simply be scaled down to a 3 mm shaft diameter device. Significant mechanical concerns exist as physical dimensions are reduced.

A computer is a machine that follows programmed instructions to perform mathematical or logical functions on input information to produce processed output information. A computer includes a logic unit that performs the mathematical or logical functions, and memory that stores the programmed instructions, the input information, and the output information. The term "computer" and similar terms, such as "processor" or "controller", encompasses both single-location and distributed implementations.

This disclosure provides improved surgical and robotic devices, systems, and methods. The inventive concepts are particularly advantageous for use with computer-assisted teleoperated surgical systems (which may be referred to as "surgical robotic systems") in which a plurality of surgical tools or instruments will be mounted on and moved by an associated plurality of robotic manipulators during a surgical procedure. The robotic systems will often comprise telerobotic, telesurgical, and/or telepresence systems that include processors configured as master-slave controllers. By providing robotic systems employing processors appropriately configured to move manipulator assemblies with articulated linkages having relatively large numbers of degrees of freedom, the motion of the linkages can be tailored for work through a minimally invasive access site. The large number of degrees of freedom may also allow a processor to position the manipulators to inhibit interference or collisions between these moving structures, and the like.

The robotic manipulator assemblies described herein will often include a robotic manipulator and a tool mounted thereon (the tool often comprising a surgical instrument in surgical versions), although the term "robotic assembly" will also encompass the manipulator without the tool mounted thereon. The term "tool" encompasses both general or industrial robotic tools and specialized robotic surgical instruments, with these later structures often including an end effector that is suitable for manipulation of tissue, treatment of tissue, imaging of tissue, or the like. The tool/manipulator interface will often be a quick disconnect tool holder or coupling, allowing rapid removal and replacement of the tool with an alternate tool. The manipulator assembly will often have a base that is fixed in space during at least a portion of a robotic procedure, and the manipulator assembly may include a number of degrees of freedom between the base and an end effector of the tool. Actuation of the end effector (such as opening or closing of the jaws of a gripping device, energizing an electrosurgical paddle, or the like) will often be separate from, and in addition to, these manipulator assembly degrees of freedom.

The end effector will typically move in the workspace with between two and six degrees of freedom. As used herein, the term "position" encompasses both location and orientation. Hence, a change in a position of an end effector (for example) may involve a translation of the end effector from a first location to a second location, a rotation of the end effector from a first orientation to a second orientation, or a combination of both.

When used for minimally invasive robotic surgery, movement of the manipulator assembly may be controlled by a processor of the system so that a shaft or intermediate portion of the tool or instrument is constrained to a safe motion through a minimally invasive surgical access site or other aperture. Such motion may include, for example, axial insertion of the shaft through the aperture site, rotation of the shaft about its axis, and pivotal motion of the shaft about a pivot point adjacent the access site, but will often preclude excessive lateral motion of the shaft which might otherwise tear the tissues adjacent the aperture or enlarge the access site inadvertently. Some or all of such constraint on the manipulator motion at the access site may be imposed using mechanical manipulator joint linkages that inhibit improper motions, or may in part or in full be imposed using robotic data processing and control techniques. Hence, such minimally invasive aperture-constrained motion of the manipulator assembly may employ between zero and three degrees of freedom of the manipulator assembly.

Many of the exemplary manipulator assemblies described herein will have more degrees of freedom than are needed to position and move an end effector within a surgical site. For example, a surgical end effector that can be positioned with six degrees of freedom at an internal surgical site through a minimally invasive aperture may in some embodiments have nine degrees of freedom (six end effector degrees of freedom—three for location, and three for orientation—plus three degrees of freedom to comply with the access site constraints), but will often have ten or more degrees of freedom. Highly configurable manipulator assemblies having more degrees of freedom than are needed for a given end effector position can be described as having or providing sufficient degrees of freedom to allow a range of joint states for an end effector position in a workspace. For example, for a given end effector position, the manipulator assembly may occupy (and be driven between) any of a range of alternative manipulator linkage positions. Similarly, for a given end effector velocity vector, the manipulator assembly may have a range of differing joint movement speeds for the various joints of the manipulator assembly.

Referring to FIGS. 1 and 2, systems for minimally invasive computer-assisted telesurgery (also referred to herein as "minimally invasive robotic surgery") can include a patient-side cart 100 and a surgeon console 40. Telesurgery is a general term for surgical systems where the surgeon uses some form of remote control, e.g., a servomechanism, or the like, to manipulate surgical instrument movements rather than directly holding and moving the instruments by hand. The robotically manipulatable surgical instruments can be inserted through small, minimally invasive surgical apertures to treat tissues at surgical sites within the patient, avoiding the trauma associated with accessing for open surgery. These robotic systems can move the working ends of the surgical instruments with sufficient dexterity to perform quite intricate surgical tasks, often by pivoting shafts of the instruments at the minimally invasive aperture, sliding of the shaft axially through the aperture, rotating of the shaft within the aperture, and/or the like.

In the depicted embodiment, the patient-side cart 100 includes a base 110, a first robotic manipulator arm assembly 120, a second robotic manipulator arm assembly 130, a third robotic manipulator arm assembly 140, and a fourth robotic manipulator arm assembly 150. Each robotic manipulator arm assembly 120, 130, 140, and 150 is pivotably coupled to the base 110. In some embodiments, fewer than four or more than four robotic manipulator arm assemblies may be included as part of the patient-side cart 100. While in the depicted embodiment the base 110 includes casters to allow ease of mobility, in some embodiments the patient-side cart 100 is fixedly mounted to a floor, ceiling, operating table, structural framework, or the like.

In a typical application, two of the robotic manipulator arm assemblies 120, 130, 140, or 150 hold surgical instruments and a third holds a stereo endoscope. The remaining robotic manipulator arm assembly is available so that another instrument may be introduced at the work site. Alternatively, the remaining robotic manipulator arm assembly may be used for introducing a second endoscope or another image capturing device, such as an ultrasound transducer, to the work site.

Each of the robotic manipulator arm assemblies 120, 130, 140, and 150 is conventionally formed of links that are coupled together and manipulated through actuatable joints. Each of the robotic manipulator arm assemblies 120, 130, 140, and 150 includes a setup arm and a device manipulator. The setup arm positions its held device so that a pivot point occurs at its entry aperture into the patient. The device manipulator may then manipulate its held device so that it may be pivoted about the pivot point, inserted into and retracted out of the entry aperture, and rotated about its shaft axis.

In the depicted embodiment, the surgeon console 40 includes a stereo vision display 45 so that the user may view the surgical work site in stereo vision from images captured by the stereoscopic camera of the patient-side cart 100. Left and right eyepieces, 46 and 47, are provided in the stereo vision display 45 so that the user may view left and right display screens inside the display 45 respectively with the user's left and right eyes. While viewing typically an image of the surgical site on a suitable viewer or display, the surgeon performs the surgical procedures on the patient by manipulating master control input devices, which in turn control the motion of robotic instruments.

The surgeon console 40 also includes left and right input devices 41, 42 that the user may grasp respectively with his/her left and right hands to manipulate devices (e.g., surgical instruments) being held by the robotic manipulator arm assemblies 120, 130, 140, and 150 of the patient-side cart 100 in preferably six degrees-of-freedom ("DOF"). Foot pedals 44 with toe and heel controls are provided on the surgeon console 40 so the user may control movement and/or actuation of devices associated with the foot pedals.

A processor 43 is provided in the surgeon console 40 for control and other purposes. The processor 43 performs various functions in the medical robotic system. One function performed by processor 43 is to translate and transfer the mechanical motion of input devices 41, 42 to actuate their respective joints in their associated robotic manipulator arm assemblies 120, 130, 140, and 150 so that the surgeon can effectively manipulate devices, such as the surgical instruments. Another function of the processor 43 is to implement the methods, cross-coupling control logic, and controllers described herein.

Although described as a processor, it is to be appreciated that the processor 43 may be implemented by any combination of hardware, software and firmware. Also, its functions as described herein may be performed by one unit or divided up among a number of subunits, each of which may be implemented in turn by any combination of hardware, software and firmware. Further, although being shown as part of or being physically adjacent to the surgeon console 40, the processor 43 may also be distributed as subunits throughout the telesurgery system.

Figure 3:
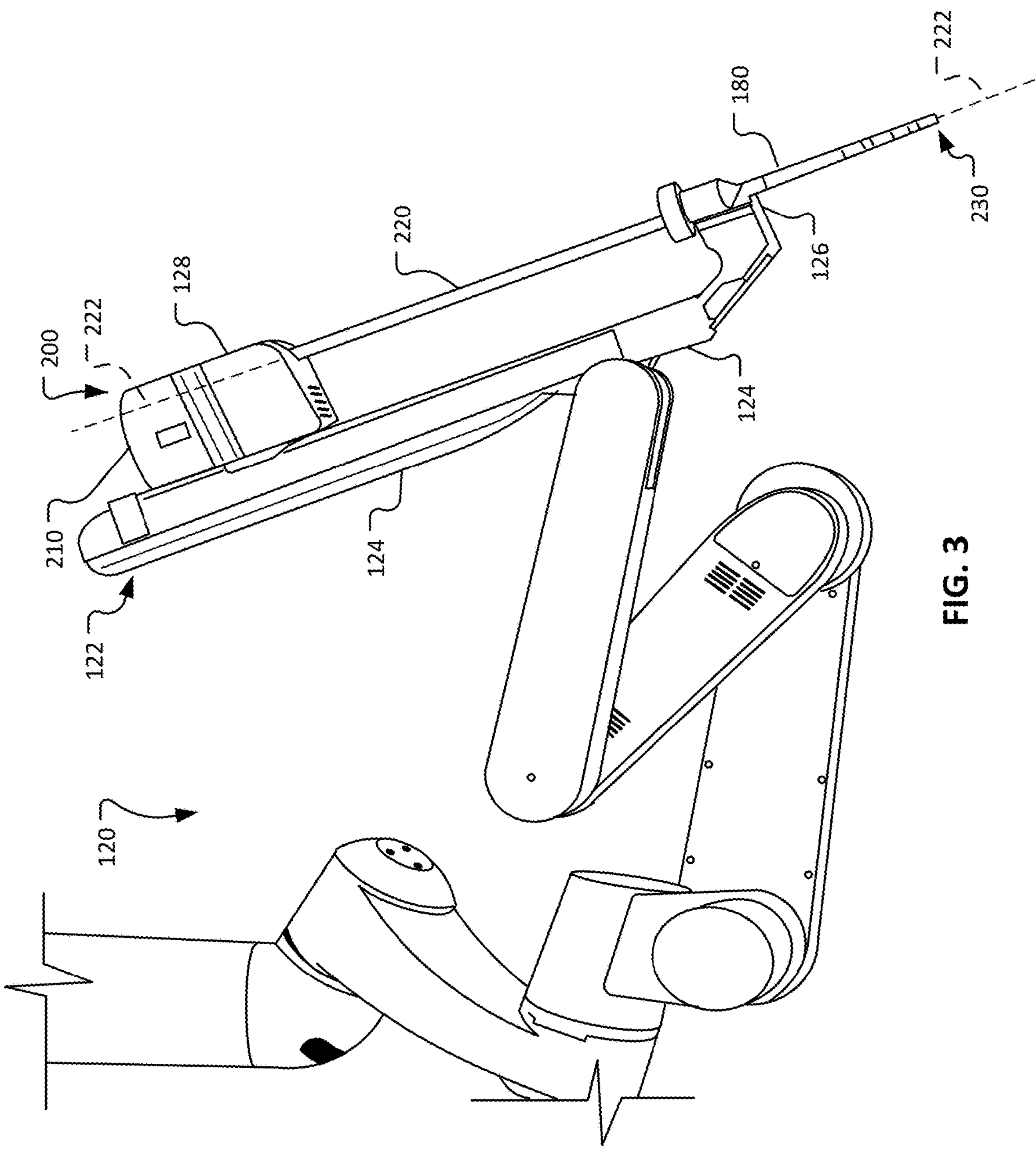
FIG. 3 is a side view of an example robotic manipulator arm assembly of a computer-assisted teleoperated surgery system.

Referring also to FIG. 3, the robotic manipulator arm assemblies 120, 130, 140, and 150 can manipulate devices such as surgical instruments to perform minimally invasive surgery. For example, in the depicted arrangement the robotic manipulator arm assembly 120 is pivotably coupled to an instrument holder 122. A cannula 180 and a surgical instrument 200 and are, in turn, releasably coupled to the instrument holder 122. The cannula 180 is a tubular member that is located at the patient interface site during a surgery. The cannula 180 defines a lumen in which an elongate shaft 220 of the surgical instrument 200 is slidably disposed. As described further below, in some embodiments the cannula 180 includes a distal end portion with a body wall retractor member.

The instrument holder 122 is pivotably coupled to a distal end of the robotic manipulator arm assembly 120. In some embodiments, the pivotable coupling between the instrument holder 122 and the distal end of robotic manipulator arm assembly 120 is a motorized joint that is actuatable from the surgeon console 40 and processor 43.

The instrument holder 122 includes an instrument holder frame 124, a cannula clamp 126, and an instrument holder carriage 128. In the depicted embodiment, the cannula clamp 126 is fixed to a distal end of the instrument holder frame 124. The cannula clamp 126 can be actuated to couple with, or to uncouple from, the cannula 180. The instrument holder carriage 128 is movably coupled to the instrument holder frame 124. More particularly, the instrument holder carriage 128 is linearly translatable along the instrument holder frame 124. In some embodiments, the movement of the instrument holder carriage 128 along the instrument holder frame 124 is a motorized, translational movement that is actuatable/controllable by the processor 43.

The surgical instrument 200 includes a transmission assembly 210, the elongate shaft 220, and an end effector 230. The transmission assembly 210 is releasably coupleable with the instrument holder carriage 128. The shaft 220 extends distally from the transmission assembly 210. The end effector 230 is coupled to a distal end of the shaft 220 by a joint mechanism (not shown in FIG. 3), which will be discussed in more detail below with respect to FIGS. 4-10.

The shaft 220 defines a longitudinal axis 222 that is coincident with a longitudinal axis of the cannula 180. As the instrument holder carriage 128 translates along the instrument holder frame 124, the elongate shaft 220 of the surgical instrument 200 is moved along the longitudinal axis 222. In such a manner, the end effector 230 can be inserted and/or retracted from a surgical workspace within the body of a patient.

Figure 4:
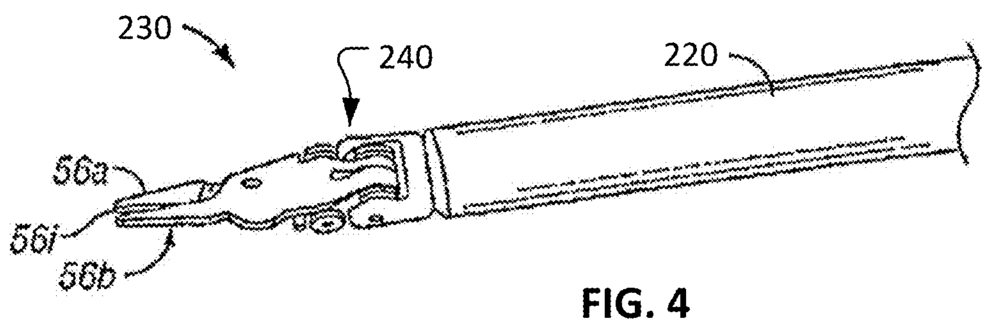
FIG. 4 is a perspective view of a distal end portion of an example surgical instrument in a first configuration.
Figure 5:
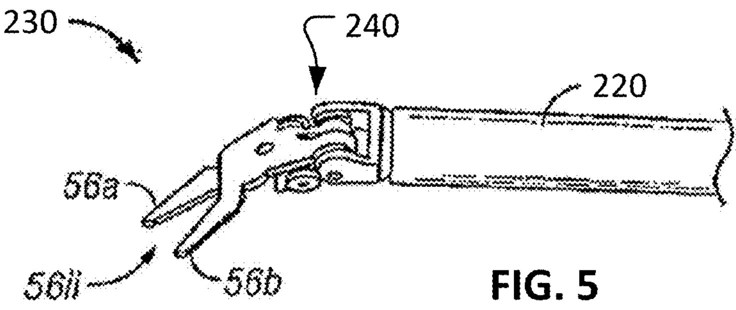
FIG. 5 is a perspective view of the distal end portion of the surgical instrument of FIG. 4 in a second configuration.
Figure 6:
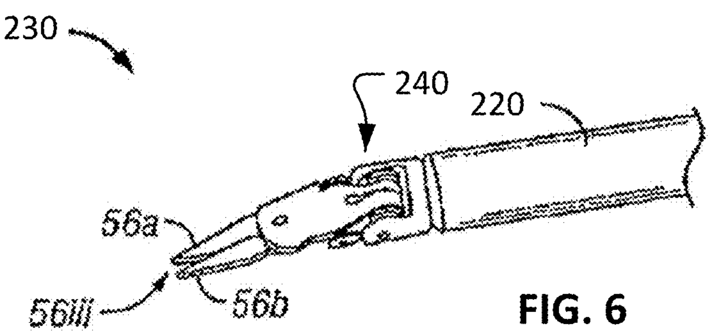
FIG. 6 is a perspective view of the distal end portion of the surgical instrument of FIG. 4 in a third configuration.

Also referring to FIGS. 4-6, a variety of alternative robotic surgical instruments of different types and differing end effectors 230 may be used, with the instruments of at least some of the manipulators being removed and replaced during a surgical procedure. Several of these end effectors, including, for example, DeBakey Forceps **56*i*, microforceps 56*ii*, and Potts scissors 56*iii* include first and second end effector elements 56*a*, 56*b* which pivot relative to each other so as to define a pair of end effector jaws. Other end effectors, including scalpels and electrocautery probes, have a single end effector element. For instruments having end effector jaws, the jaws will often be actuated by squeezing the grip members of input devices 41, 42**.

The end effector 230 is coupled to a distal end of the shaft 220 by a joint mechanism 240, which provides a pivotable configuration with one, two, three, four or more degrees of freedom by which an orientation of the end effector 230 can be adjusted. The elongate shaft 220 allows the end effector

230 and the distal end of the shaft 220 to be inserted distally into a surgical worksite through a minimally invasive aperture (via cannula 180; FIG. 3), often through a body wall (e.g., abdominal wall) or the like. In some cases, a body wall retractor member on a distal end of the cannula 180 can be used to tent the body wall, thereby increasing the surgical workspace size. In some cases, the surgical worksite may be insufflated, and movement of the end effectors 230 within the patient will often be effected, at least in part, by pivoting of the instruments 200 about the location at which the shaft 220 passes through the minimally invasive aperture. In other words, the robotic manipulator arm assemblies 120, 130, 140, and 150 will move the transmission assembly 210 outside the patient so that the shaft 220 extends through a minimally invasive aperture location so as to help provide a desired movement of end effector 230. Hence, the robotic manipulator arm assemblies 120, 130, 140, and 150 will often undergo significant movement outside patient during a surgical procedure.

Figure 7:
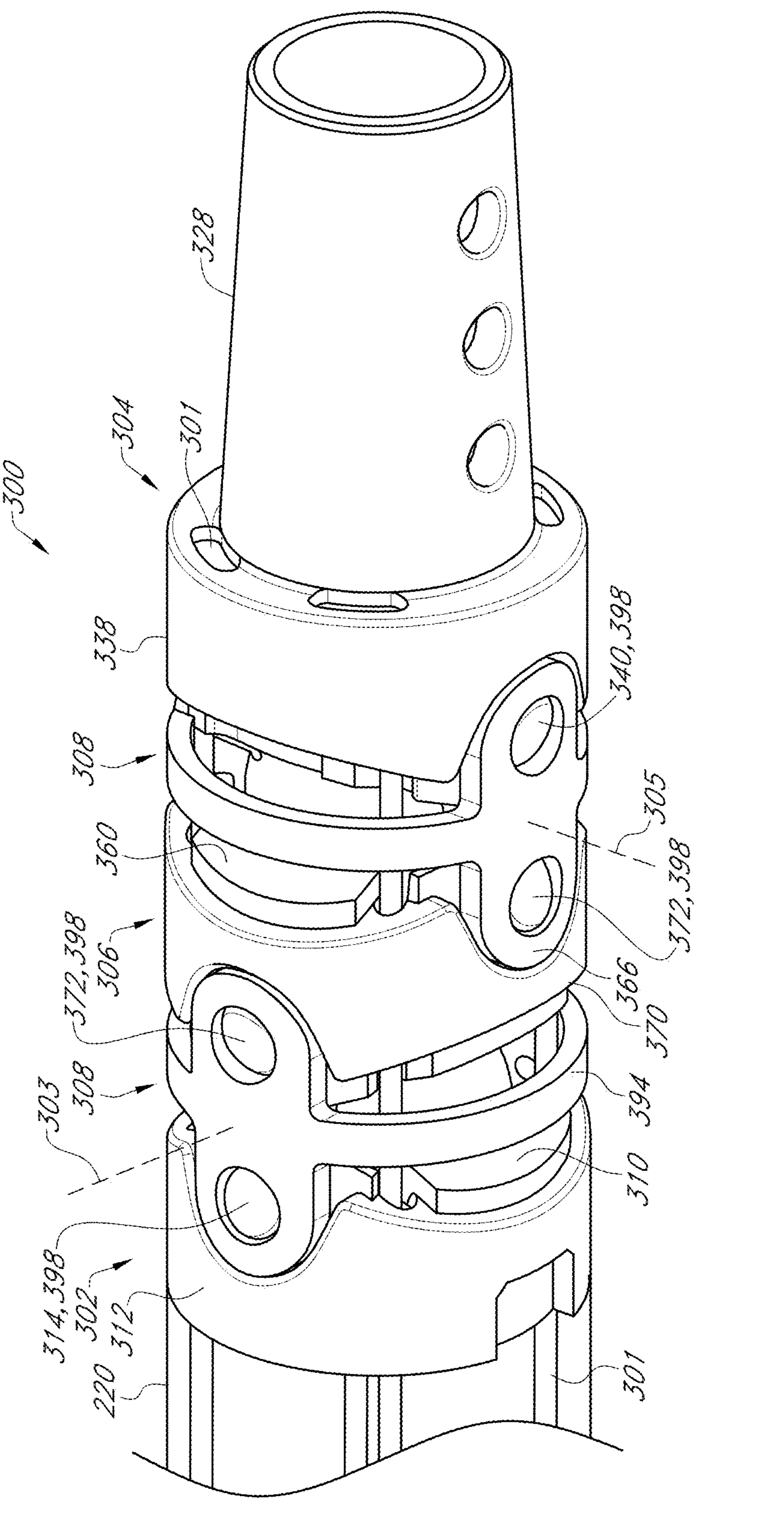
FIG. 7 is a perspective view of a distal end portion of a surgical instrument including an example joint mechanism and surgical tool or end effector.

Referring to FIG. 7, a joint mechanism 300 may be used as an alternative to the joint mechanism 240 to moveably couple a variety of types of end effectors to the shaft 220 of a surgical instrument. Such end effectors may include the end effector 230 of FIGS. 4-6, end effectors (e.g., gripper jaws) that are similar to the end effector 230, or other end effectors, such as a cauterizer, a camera, a stapler, a cutting device, or a suction device, to provide a few examples. The joint mechanism 300 is pivotable about two axes 303, 305 that are perpendicular to each other to allow movement of an end effector with respect to the shaft 220 (e.g., corresponding to two degrees of freedom), as will be discussed in more detail below. In some cases, joint mechanism 300 can be designed to have three or more degrees of freedom.

The joint mechanism 300 includes a first end joint member 302 that is engageable, coupleable, or attachable to a distal end of the shaft 220, a second end joint member 304 that is coupled to an end effector, and a middle joint member 306 disposed between and coupled to both the first and second end joint members 302, 304. The joint mechanism 300 further includes two linkage members 308 that respectively, pivotably couple the first end joint member 302 to the middle joint member 306 and pivotably couple the second end joint member 304 to the middle joint member 306.

Figure 8:
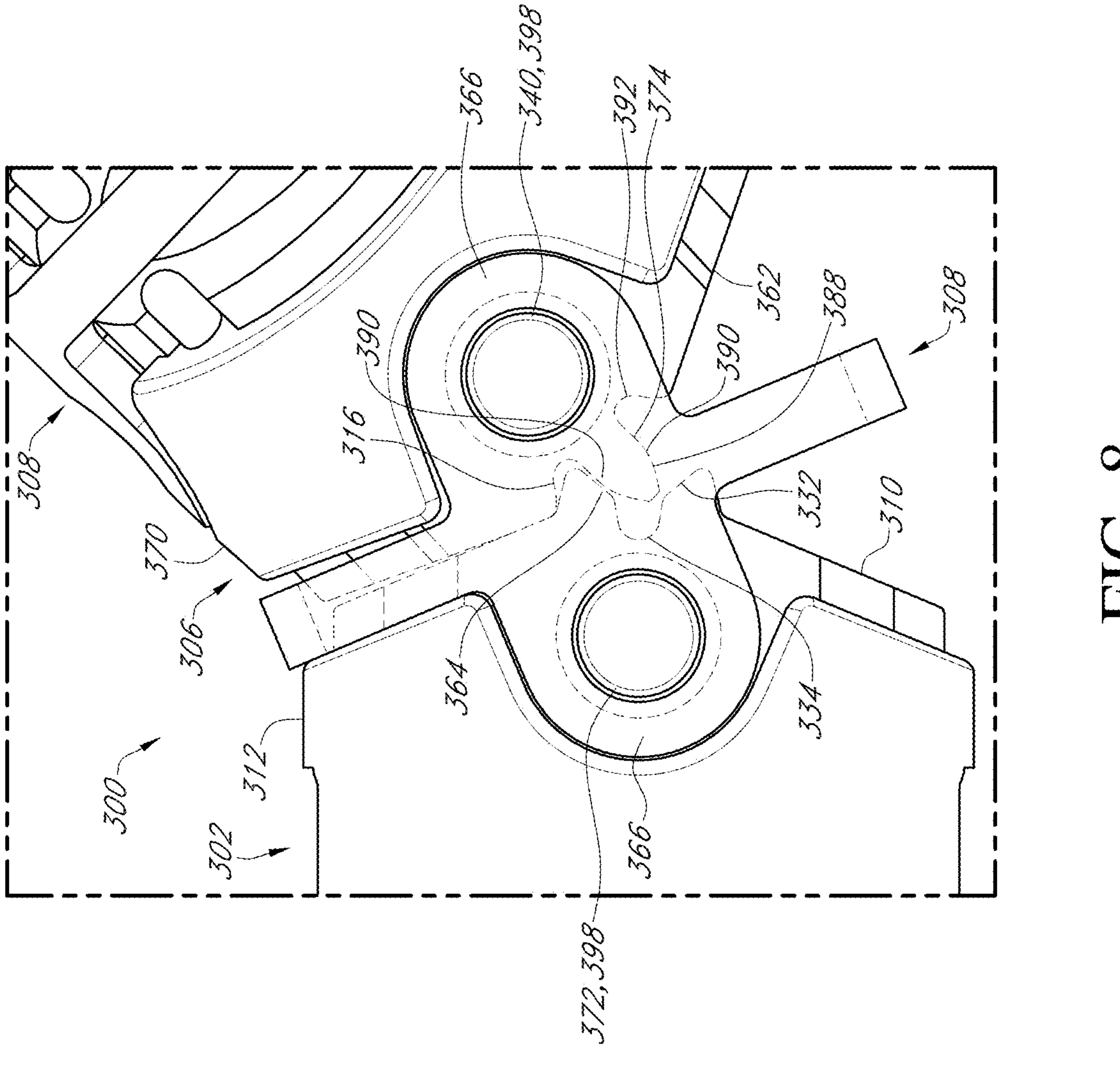
FIG. 8 is a side view of a portion of the joint mechanism of FIG. 7 in a deflected arrangement.
Figure 9:
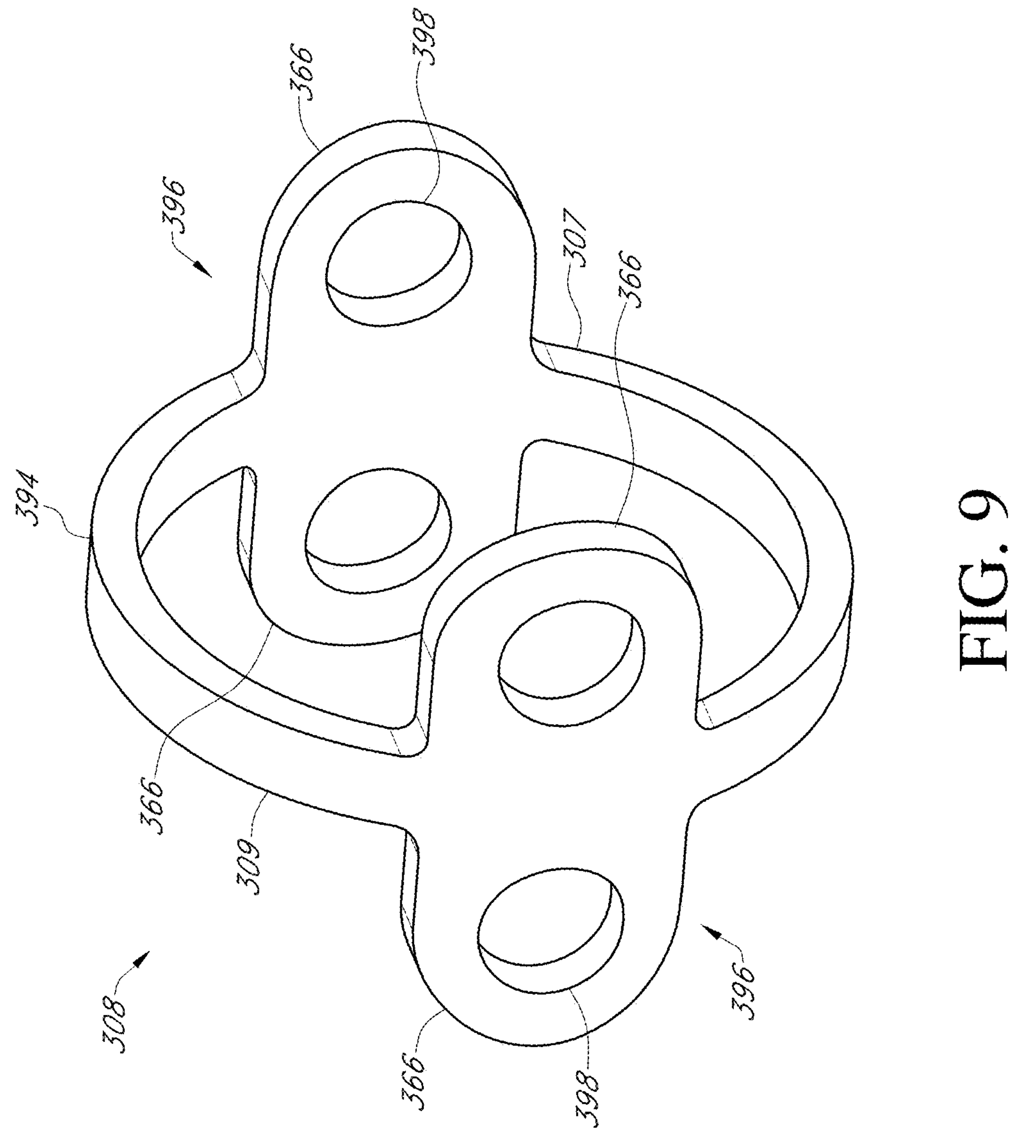
FIG. 9 is a perspective view of a linkage member component of the joint mechanism of FIG. 7.
Figure 10:
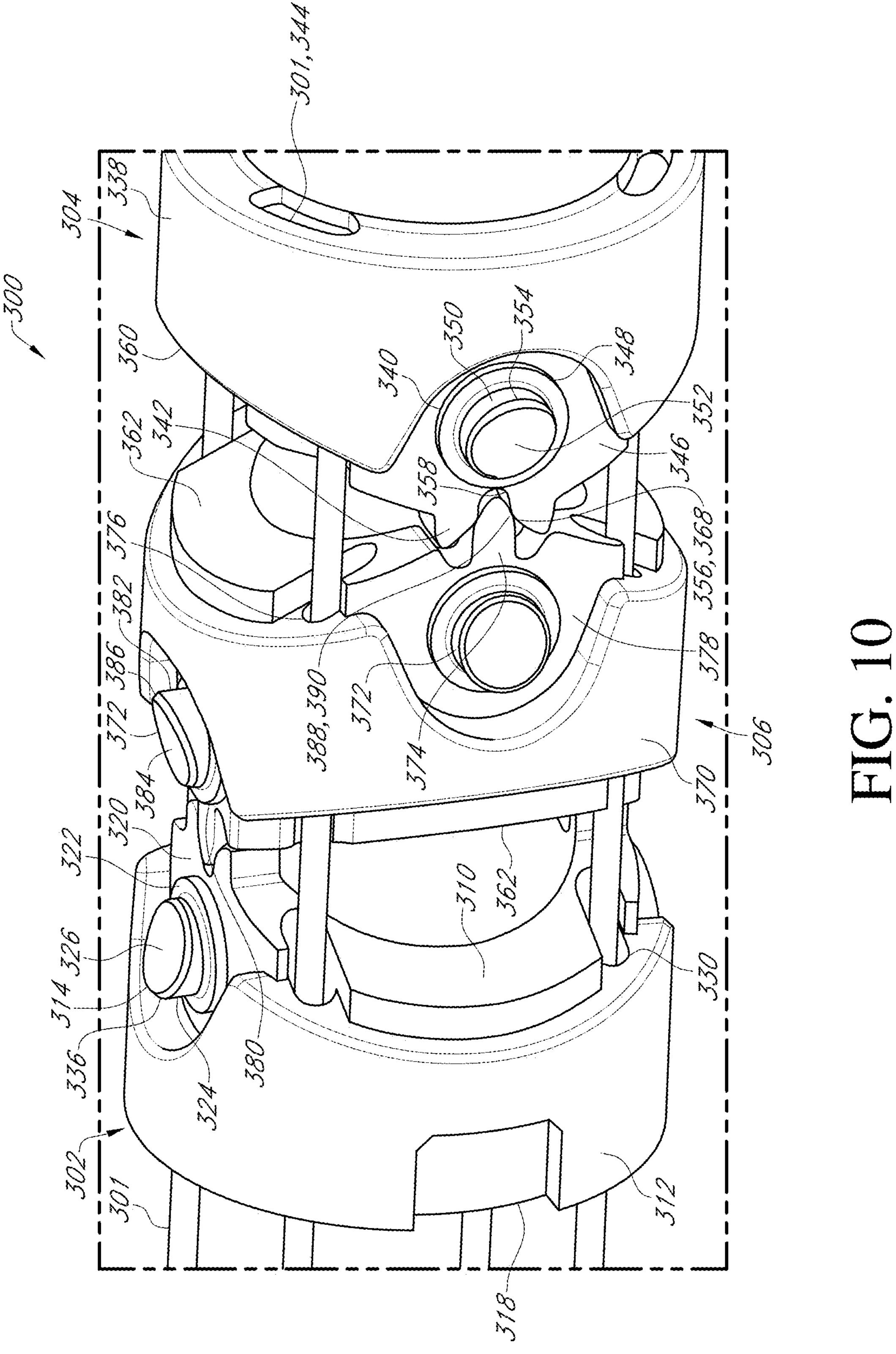
FIG. 10 is a perspective view of the joint mechanism of FIG. 7 with the linkage members removed to provide enhanced visualization of internal structures of the joint mechanism.

Also referring to FIGS. 8-10, the depicted embodiment of the first end joint member 302 includes a generally tubular wall 312, two radially-extending protrusions 314 located along opposite sides of the tubular wall 312 (e.g., spaced about 180 degrees apart), two pairs of gear teeth 316 respectively associated with the two protrusions 314, and two abutment surfaces 310 that extend along arcuate paths between the two pairs of gear teeth 316. The tubular wall 312 defines two opposing notches 318 by which the first end joint member 302 can be coupled with the shaft 220, and four longitudinally extending channels 330 through which two respective cables 301 pass to couple the joint mechanism 300 to the surgical instrument 200 and to transmit forces to actuate movements of the joint mechanism 300. The tubular wall 312 further defines two opposing recesses 320 in which the two protrusions 314 are respectively positioned and from which the two pairs of gear teeth 316 respectively extend longitudinally. Each protrusion 314 includes a circumferential shoulder 322 positioned along a respective recess 320 and an extension piece 324 that extends radially from the shoulder 322. The shoulders 322 and the extension pieces 324 have circular cross-sectional shapes, and the extension pieces 324 have respective flat surfaces 326 that are oriented at an acute angle with respect to a central longitudinal axis of the first end joint member 302. The flat surfaces 326 of the extension pieces 324 are circumferentially surrounded by respective beveled edges 336. The beveled edges 336 can facilitate assembly of the first end joint member 302 with a respective linkage member 308, as will be discussed in more detail below. In some embodiments, the protrusions 314 are spaced about 90 degrees from the notches 318 about the tubular wall 312.

Each gear tooth 316 has a curved or contoured surface 332 that makes contact with a portion of the middle joint member 306, and each pair of adjacent teeth 316 defines a pocket 334 (e.g., a valley) that can receive such portion of the middle joint member 306, as will be discussed in more detail below. Additionally, the abutment surfaces 310 are oriented at an acute angle with respect to the central longitudinal axis of the first end joint member 302 for contacting complementary portions of the middle joint member 306, as will be discussed in more detail below.

The depicted embodiment of the second end joint member 304 includes a generally tubular wall 338, two radially-extending protrusions 340 located along opposite sides of the tubular wall 338 (e.g., spaced about 180 degrees apart), two pairs of gear teeth 342 respectively associated with the protrusions 340, and two abutment surfaces 360 that extend along arcuate paths between the two pairs of gear teeth 342. The tubular wall 338 defines two opposing channels 344 through which the respective cables 301 pass to couple the joint mechanism 300 to the surgical instrument 200 and to transmit forces to actuate movements of the joint mechanism 300. The tubular wall 338 further defines two opposing recesses 346 in which the two protrusions 340 are respectively positioned and from which the two pairs of gear teeth 342 respectively extend longitudinally. Each protrusion 340 includes a circumferential shoulder 348 positioned along the recess 346 and an extension piece 350 that extends radially from the shoulder 348. The shoulders 348 and the extension pieces 350 have circular cross-sectional shapes, and the extension pieces 350 have respective flat surfaces 352 that are oriented at an acute angle with respect to a central longitudinal axis of the second end joint member 304. The flat surfaces 352 of the extension pieces 350 are circumferentially surrounded by respective beveled edges 354. The beveled edges 354 can facilitate assembly of the second end joint member 304 with a respective linkage member 308, as will be discussed in more detail below. In some embodiments, the protrusions 340 are spaced about 90 degrees from centers of the channels 344 about the tubular wall 338.

Each gear tooth 342 has a curved or contoured surface 356 that makes contact with a portion of the middle joint member 306, and each pair of adjacent teeth 342 defines a pocket 358 (e.g., a valley) that can receive the portion of the middle joint member 306, as will be discussed in more detail below. Additionally, the abutment surfaces 360 are oriented at an acute angle with respect to the central longitudinal axis of the second end joint member 304 for contacting complementary portions of the middle joint member 306, as will be discussed in more detail below.

The second end joint member 304 further includes a distal end piece 328 that represents an end effector (a suction device in this example, although any suitable end effector can be incorporated). The distal end piece 328 extends longitudinally (distally) from the tubular wall 338 and has a generally frustoconical shape.

The depicted embodiment of the middle joint member 306 includes a generally tubular wall 370, two sets of two radially-extending protrusions 372 located along opposite sides of the tubular wall 370, two gear teeth 374 respectively associated with each set of protrusions 372, and two sets of abutment surfaces 362 that respectively extend along arcuate paths between opposite gear teeth 374. The two sets of protrusions 372 are located along opposite ends of the middle joint member 306 and are spaced apart from each other by about 90 degrees about the tubular wall 370. The two sets of abutment surfaces 362 are located along opposite ends of the middle joint member 306. The tubular wall 370 defines four longitudinally extending channels 376 through which the two respective cables 301 pass to couple the joint mechanism 300 to the surgical instrument 200 and to transmit forces to actuate movements of the joint mechanism 300. The tubular wall 370 further defines two sets of two opposing recesses 378 in which the two sets of protrusions 372 are respectively positioned and from which the sets of two gear teeth 374 respectively extend longitudinally. Each protrusion 372 includes a circumferential shoulder 380 positioned along a respective recess 378 and an extension piece 382 that extends radially from the shoulder 380. The shoulders 380 and the extension pieces 382 have circular cross-sectional shapes, and the extension pieces 382 have respective flat surfaces 384 that are oriented at an acute angle with respect to a central longitudinal axis of the middle joint member 306. The flat surfaces 384 of the extension pieces 382 are circumferentially surrounded by respective beveled edges 386. The beveled edges 386 can facilitate assembly of the middle joint member 306 with the linkage members 308, as well be discussed in more detail below.

Each gear tooth 374 has a curved or contoured surface 388 that make contact with portions of the respective gear teeth 316, 342 of the first or second joint member 302, 304. Additionally, each gear tooth 374, together with the tubular wall 370, defines two opposing pockets 392 (e.g., valleys) that can receive the respective gear teeth 316, 342 of the first or second joint member 302, 304, as will be discussed in more detail below. The abutment surfaces 362 are oriented at an acute angle with respect to the central longitudinal axis of the middle joint member 306 for respectively contacting the abutment surfaces 310, 360 of the first and second end joint members 302, 304, as will be discussed in more detail below. Each gear tooth 374 of the middle joint member 306 and a respective pair of gear teeth 316, 342 of the first or second end joint members 302, 304 form a gear that couples the middle joint member 306 to the first or second end joint member 302, 304. The gears permit pivotal movement of the middle joint member 306 with respect to the first and second end joint members 302, 304, but prevent lateral movement of the middle joint member 306 with respect to the first and second end joint members 302, 304.

Referring to FIG. 9 in particular, in the depicted embodiment, the linkage members 308 (of which two are included as components of the joint mechanism 300) are structurally identical and are oriented at about 90 degrees from each other along a circumference of middle joint member 306. One linkage member 308 couples the first end joint member 302 to the middle joint member 306, and the other linkage member 308 couples the second end joint member 304 to the middle joint member 306. Each linkage member 308 is a unitary component that integrally includes an annular band 394 and two pairs 396 of bosses 366 that protrude longitudinally from the annular band 394. Each pair 396 of bosses 366 includes a first boss 366 that extends in a first longitudinal direction from a first end 307 of the annular band 394 and a second boss 366 that extends in a second, opposite longitudinal direction from a second, opposite end 309 of the annular band 394. The two pairs 396 of bosses 366 are spaced about 180 degrees apart from each other around a circumference of the annular band 394 (i.e., the two pairs 396 of bosses 366 are positioned along opposite sides of the annular band 394. Each boss 366 defines a hole 398 that is sized to receive a protrusion 314, 340, 372 of the first end, second end, and middle joint members 302, 304, 306. The beveled edges 336, 354, 386 of the protrusions 314, 340, 372, and the inclined flat surfaces 326, 352, 384 facilitate passage of the protrusions 314, 340, 372 through and seating of the protrusions 314, 340, 372 within the holes 398 of the bosses 366. Furthermore, the shoulders 322, 348, 380 of the protrusions 314, 340, 372 provide rotational bearing surfaces for the bosses 366. The annular bands 394 have a diameter that is large enough to surround (e.g., encompass) the cables 301 that pass through respective passages defined by channels (not shown) along the elongate shaft 220, the channels 330, 344, 376, of the first end, the second end, and the middle joint members 302, 304, 306.

The first end joint member 302 and the middle joint member 306 can pivot with respect to each other about the axis 303. The axis 303 is a moving axis that remains along a central plane that bisects the annular band 394. A position of the axis 303 is determined by points of contact between the pairs of gear teeth 316 and the respective gear teeth 374 (i.e., the position of the axis 303 is determined by orientations of the first end joint member 302 and the middle joint member 306). Similarly, the second end joint member 304 and the middle joint member 306 can pivot with respect to each other about the axis 305. The axis 305 is a moving axis that remains along a central plane that bisects the annular band 394. A position of the axis 305 is determined by points of contact between the pairs of gear teeth 342 and the respective gear teeth 374 (i.e., the position of the axis 305 is determined by orientations of the second end joint member 304 and the middle joint member 306).

The linkage members 308 maintain engagement between the gear teeth 316, 342 of the first and second end joint members 302, 304 and the gear teeth 374 of the middle joint member 306 such that at any orientations of the first, second, and middle joint members 302, 304, 306, the gear teeth 374 of the middle joint member 306 remain within respective pockets 334, 358 of the first and second end joint members 302, 304, and the gear teeth 316, 342 of the first and second joint end members 302, 304 remain associated with the respective pockets 392 of the middle joint member 306 without reliance solely on the tensile force from the cables 301. In some embodiments, contact between inner edge surfaces of the bosses 366 defining the holes 398 and the outer surfaces of the protrusions 314, 340, 372 and/or contact between outer edge surfaces of the bosses 366 and inner edge surfaces of the recesses 320, 346, 378 can act as load bearing surfaces to counteract tension that may be exerted between the joint members 302, 304, 306 and the linkage members 308 during movement of the joint mechanism 300. Such contact can further prevent lateral and axial movements of the joint members 302, 304, 306 with respect to each other.

Referring particularly to FIG. 8 (that illustrates the engagement between the first end joint member 302 and the middle joint member 306 as an example), at least one inner contact points 364, 368 along the curved surface 332, 356 of a gear tooth 316, 342 of the first and second joint members 302, 304 remains in contact with at least one respective outer contact point 390 along the curved surface 388 of the respective gear tooth 374 at all orientations of the first, second, and middle joint members 302, 304, 306. For example, as shown in the pivoted joint configuration of FIG. 8, one inner contact point 364 of one gear tooth 316 is in contact with one outer contact point 390 of the gear tooth 374. Referring to the linear (e.g., in-line) joint configuration of the second end joint member 304 and the middle joint member 306 of FIG. 10, two inner contact points 368 of a set of two gear teeth 342 are in contact with two outer contact points 390 along the curved surface 388 of the respective gear tooth 374.

In a fully pivoted joint configuration (e.g., shown in FIG. 8), the abutment surfaces 310, 360 of the first and second joint end members 302, 304 abut respective abutment surfaces 362 of the middle joint member 306, whereas in the linear configuration (shown in FIG. 10), the abutment surfaces 310, 360 of the first and second joint end members 302, 304 are spaced apart from respective abutment surfaces 362 of the middle joint member 306. Proximal ends (not shown) of the two cables 301 are coupled to two respective capstans (not shown) located at proximal ends of the elongate shaft 220. Owing to the two contact points (e.g., the outer contact points 390) between the gear teeth 374 of the middle joint member 306 and respective inner contact points (e.g., the inner contact points 364, 368) of the gear teeth 316, 342 of the first and second end joint member 302, 304, as the first or second end joint member 302, 304 pivots with respect to the middle joint member 306, one proximal end of a cable 301 is paid out (e.g., extended distally) by the capstan, while another proximal end of the same cable 301 is pulled in (e.g., pulled proximally) by the respective capstan, such that a total operational length of the cable 301 is maintained to effect link conservation. Accordingly, the cables 301 are prevented from becoming over-tensioned and/or slackened during operations of the joint mechanism 300.

The joint mechanism 300 is scalable to any suitable size. For example, in some embodiments the components of the joint mechanism 300 can be sized, without limitation, as follows. In some embodiments, the joint members 302, 304, 306 have an outer diameter (e.g., defined by the tubular walls 312, 338, 370) of about 0.5 cm to about 1.0 cm and inner diameter of about 0.2 cm to about 0.7 cm. In some embodiments, the protrusions 314, 340, 372 have a maximum length (e.g., extending from the recesses 320, 346, 378) of about 0.05 cm to about 0.1 cm and have a minimum length (e.g., extending from the recesses 320, 346, 378) of about 0.03 cm to about 0.08 cm, such that the flat surfaces 326, 352, 386 of the protrusions 314, 340, 372 are oriented at an angle of about −5 degrees to about 30 degrees from central axes of the respective joint members 302, 304, 306. In some embodiments, the shoulders 322, 348, 380 of the protrusions 314, 340, 372 have a diameter of about 4 cm to about 8 cm and have a thickness of about 0.1 cm to about 0.4 cm. In some embodiments, the extension pieces 324, 350, 382 of the protrusions 314, 340, 372 have a diameter of about 0.1 cm to about 0.2 cm and have a length (e.g., extending from the shoulders 322, 348, 380) of about 0.05 cm to about 0.2 cm.

In some embodiments, the linkage members 308 have an outer diameter of about 0.5 cm to about 1.0 cm and an inner diameter of about 0.4 cm to about 0.9 cm. In some embodiments, the bosses 366 of the linkage members 308 have a length (e.g., with respect to the ends 307, 309 of the annular bands 394) of about 0.3 cm to about 0.5 cm. In some embodiments, the holes 398 defined by the bosses 366 have a diameter of about 0.1 cm to about 0.2 cm.

The joint members 302, 304, 306 are typically made of one or more metallic or polymeric materials, such as, but not limited to, polycarbonate, polyetherimide (PEI), Polysulphone (PSU), Polyphthalamide (PPA), Polyether ether ketone (PEEK). The joint members 302, 304, 306 may be manufactured via one or more techniques, such as, but not limited to, by injection molding or machining. The linkage members 308 are typically made of one or more metallic or polymeric materials, such as, but not limited to, stainless steel, titanium, aluminum, or the aforementioned polymeric materials. The linkage members 308 may be manufactured via one or more techniques, such as, but not limited to, injection molding, laser cutting, or electrical discharge machining (EDM).

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous. Additionally, while the components of the joint mechanism 300 have been described as having certain shapes and dimensions, in some embodiments, joint mechanisms that are similar in construction and function to the joint mechanism 300 may include similar components that have one or more shapes and/or dimensions that are different from those of the joint mechanism 300.

What is claimed is:

1. A joint mechanism, comprising:

a first joint member and a second joint member each defining a radial dimension and a longitudinal dimension, wherein the first joint member comprises:

a first pair of joint features extending in the longitudinal dimension, the first pair of joint features located diametrically opposite each other, a second pair of joint features at a location along the radial dimension of the first joint member in alignment with the first pair of joint features, respectively, the second pair of joint features located diametrically opposite each other;

wherein the second joint member comprises:

a third pair of joint features extending in the longitudinal dimension, the third pair of joint features located diametrically opposite each other, a fourth pair of joint features located at a location along the radial dimension of the second joint member in alignment with the third pair of joint features, respectively, the fourth pair of joint features located diametrically opposite each other; and a linkage member pivotably coupled to each of the second pair and fourth pair of joint features, wherein the first pair of joint features and the third pair of joint features are complementary and in mating engagement with each other, wherein the first pair and third pair of joint features define an axis of rotation, and the first joint member and second joint member are configured to articulate relative to each other about the axis of rotation, and wherein the linkage member comprises an annular band encircling a region between the first joint member and the second joint member.

2. The joint mechanism of claim 1, wherein each of the first pair of joint features comprise a first gear surface profile and each of the third pair of joint features comprise a second gear surface profile.

3. The joint mechanism of claim 1, wherein the linkage member further comprises:

a plurality of bosses extending longitudinally from the annular band and respectively pivotably coupled to the second and fourth pairs of joint features.

4. The joint mechanism of claim 3, wherein the joint features of the second and fourth pairs of joint features comprise radially extending protrusions, and wherein the bosses of the plurality of bosses comprise openings configured to receive the respective radially extending protrusions.

5. The joint mechanism of claim 3, wherein the joint features of the second and fourth pairs of joint features comprise openings, and wherein the bosses of the plurality of bosses comprise radially extending protrusions configured to be received by respective openings.

6. The joint mechanism of claim 1, wherein the axis of rotation is moveable along a central plane bisecting the annular band of the linkage member in response to a relative orientation of the first and third pairs of joint features.

7. The joint mechanism of claim 1, wherein the linkage member exerts a force maintaining engagement of the first pair of joint features and the third pair of joint features through a range of relative articulation of the first joint member and second joint member about the axis of rotation.

8. The joint mechanism of claim 1, wherein each of the first and second joint members is generally tubular shaped with a central passage.

9. The joint mechanism of claim 8, wherein the first joint member comprises a first pair of abutment surface portions extending between the second pair of joint features, and wherein the second joint member comprises a second pair of abutment surface portions extending between the fourth pair of joint features, and wherein in a neutral position of articulation of the first and second joint members, the first pair of abutment surface portion and the second pair of abutment surfaces are longitudinally spaced from each other, and wherein in a fully articulated position of the first and second joint members, one of the first pair of abutment surface portions and one of the second pair of abutment surfaces contact each other.

10. A surgical instrument, comprising:

an elongate shaft; and a joint mechanism coupled to a distal end of the elongate shaft, the joint mechanism comprising:

a first joint member and a second joint member each defining a radial dimension and a longitudinal dimension, wherein the first joint member comprises:

a first pair of joint features extending in the longitudinal dimension and located diametrically opposite each other; and a second pair of joint features located along the radial dimension of the first joint member such that the second pair of joint features are aligned with the first pair of joint features, wherein the second pair of joint features are located diametrically opposite each other;

wherein the second joint member comprises:

a third pair of joint features extending in the longitudinal dimension and located diametrically opposite each other; and a fourth pair of joint features located along the radial dimension of the second joint member such that the fourth pair of joint features are aligned with the third pair of joint features, wherein the fourth pair of joint features are located diametrically opposite each other; and a linkage member pivotably coupled to each of the second pair and fourth pair of joint features, wherein the linkage member comprises an annular band encircling a region between the first joint member and the second joint member.

11. The surgical instrument of claim 10, further comprising two cables extending along the elongate shaft and coupling the joint mechanism thereto.

12. The surgical instrument of claim 11, wherein the cables extend through passages defined in a wall of the first joint member.

13. The surgical instrument of claim 10, further comprising an end effector coupled to the distal end of the elongate shaft by the joint mechanism.

14. The surgical instrument of claim 13, wherein:

the second joint member further comprises a distal end piece; and the end effector is coupled to the distal end of the elongate shaft at the distal end piece of the second joint member.

15. The surgical instrument of claim 10, wherein the first pair of joint features and the third pair of joint features are complimentary and in mating engagement with one another.

16. The surgical instrument of claim 15, wherein:

the first pair and third pair of joint features define an axis of rotation; and the first joint member and the second joint member are configured to articulate relative to each other about the axis of rotation.

17. The surgical instrument of claim 10, wherein the linkage member further comprises:

a plurality of bosses extending longitudinally from the annular band and respectively pivotably coupled to the second and fourth pairs of joint features.

18. The surgical instrument of claim 10, wherein the linkage member is configured to pivot relative to each of the second pair and fourth pair of joint features in response to articulation of the first joint member and the second joint member relative to each other.

19. The surgical instrument of claim 10, wherein the linkage member exerts a force maintaining engagement of the first pair of joint features with the third pair of joint features through a range of articulation of the first joint member and second joint member relative to each other.

20. The surgical instrument of claim 10, wherein:

each joint feature of the first pair of joint features comprises a first gear surface profile and each joint feature of the third pair of joint features comprises a second gear surface profile; and the first gear surface profile and the second gear surface profile are complimentary surface profiles.

* * * * *